United States Patent [19]

Siczek

[11] Patent Number: 5,048,069
[45] Date of Patent: Sep. 10, 1991

[54] DUAL-SLIDE SUPPORT MECHANISM FOR X-RAY SYSTEM COMPONENTS

[75] Inventor: Bernard W. Siczek, Boulder, Colo.
[73] Assignee: Fischer Imaging Corporation, Denver, Colo.
[21] Appl. No.: 493,243
[22] Filed: Mar. 14, 1990
[51] Int. Cl.$^5$ .............................................. H05G 1/02
[52] U.S. Cl. ................................... 378/197; 378/193; 378/196
[58] Field of Search ............... 378/197, 196, 193, 195, 378/198

[56] References Cited

U.S. PATENT DOCUMENTS

| | | | |
|---|---|---|---|
| 3,976,885 | 8/1976 | Brunnett et al. | 378/197 |
| 4,358,856 | 11/1982 | Stivender et al. | 378/197 |
| 4,363,128 | 12/1982 | Grady et al. | 378/197 |
| 4,635,284 | 1/1987 | Christiansen | 378/197 |
| 4,741,015 | 4/1988 | Charrier | 378/197 |
| 4,866,751 | 9/1989 | Louiday | 378/197 |
| 4,884,293 | 11/1989 | Koyama | 378/197 |

*Primary Examiner*—Edward P. Westin
*Assistant Examiner*—Kim-Kwok Chu
*Attorney, Agent, or Firm*—William E. Hein

[57] ABSTRACT

A bi-directional dual-slide support mechanism providing support and extended travel for X-ray system components, such as an image intensifier, includes a primary slide driven bi-directionally over a primary range of travel by a motorized rack and pinion arrangement and a secondary slide in telescoping relationship with the primary slide driven bi-directionally in concert with the primary slide by stationary belts coupled over roller members positioned at opposite ends of the primary slide, the belts being secured to a fixed frame member and to the secondary slide.

4 Claims, 5 Drawing Sheets

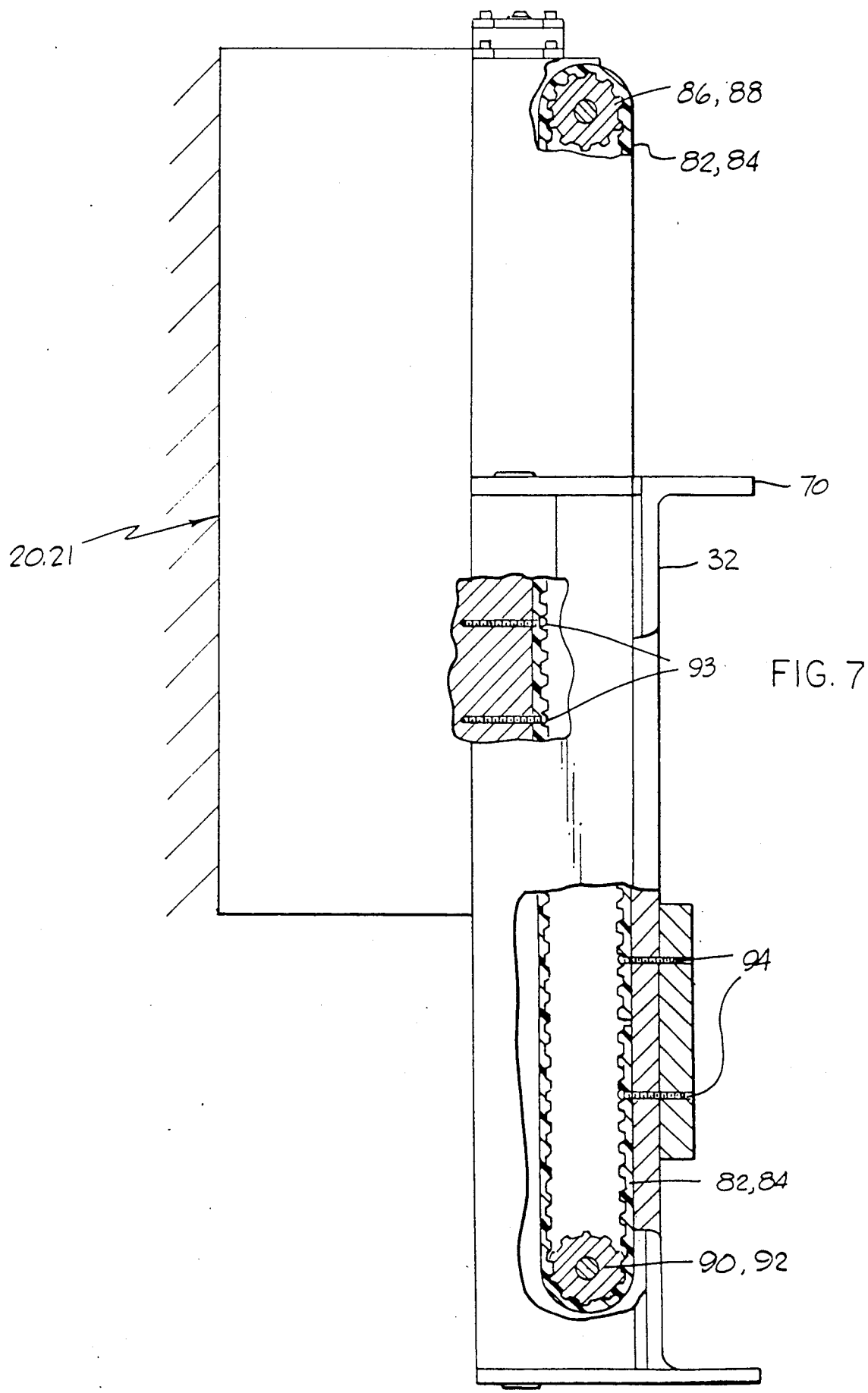

DUAL-SLIDE SUPPORT MECHANISM FOR X-RAY SYSTEM COMPONENTS

BACKGROUND AND SUMMARY OF THE INVENTION

This invention relates generally to X-ray imaging systems of the type employed for performing various X-ray examination procedures, including positioning for lithrotripsy, and more specifically to a dual-slide support mechanism for permitting extended travel of image intensifier and X-ray tub components of such systems. Known X-ray imaging systems employ a C-shaped arm, encompassing a patient table, for supporting an image intensifier and an X-ray tube in alignment with each other at opposing ends of the C-shaped arm. These prior art X-ray imaging systems provide for only 8-12 inches of travel of the image intensifier, for example, based upon the restriction that the support mechanism providing travel not extend beyond the ends of the image intensifier itself when the image intensifier is positioned in the center of its permitted range of travel. Since the amount of X-ray radiation required to perform a specific procedure increases as the cube of the distance between the patient and the image intensifier, it is important, in order to minimize the amount of X-ray radiation to which the patient is exposed, to position the image intensifier as near the patient as possible. Additional travel of the image intensifier is also required for parking the image intensifier in bi-plane X-ray imaging systems. It is also necessary, in some applications, to position the image intensifier underneath the patient table, thereby also requiring greater travel of the image intensifier than is possible in prior art X-ray imaging systems. These requirements dictate that the image intensifer be permitted to travel over a range of approximately 18-24 inches, or nearly double the range of travel that is possible in prior art image intensifier support systems. However, this extended range of travel of the image intensifier must be obtained through use of a support mechanism whose overall length is no greater than the overall length of the image intensifier itself when the image intensifier is positioned in the center of its permitted range of travel.

It is therefore a principal object of the present invention to provide an image intensifier support mechanism in which the image intensifier is supported for bi-directional travel over an extended range in a manner that insures its mechanical rigidity and stability over the entire range of travel and that does not allow the support mechanism to extend beyond either end of the image intensifier when the image intensifier is positioned in the center of its permitted range of travel. This and other objects are accomplished in accordance with the illustrated preferred embodiments of the present invention by providing a dual slide support mechanism in which a primary slide is bi-directionally driven over a primary range of travel by a rack and pinion arrangement and in which a secondary slide in telescoping relationship with the primary slide is bi-directionally driven in concert with the primary slide by stationary belts coupled over and under the primary slide between a fixed frame member and the secondary slide.

BRIEF DESCRIPTION OF THE DRAWINGS

FIG. 7 is a partial sectional side view of the dual-slide image intensifier support mechanism of FIGS. 1-5.

DETAILED DESCRIPTION OF THE INVENTION

Figure 1:
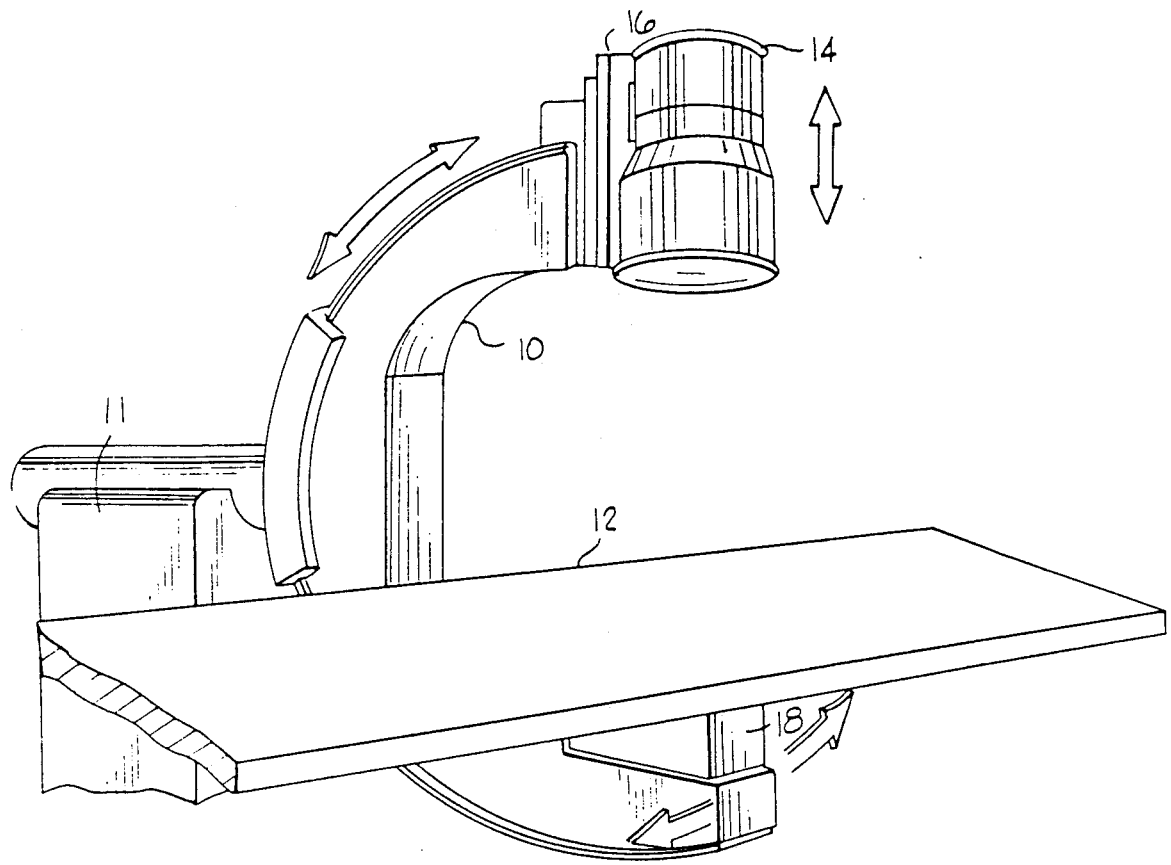
FIG. 1 is a front pictorial diagram of a portion of an X-ray imaging system employing a dual-slide image intensifier support mechanism constructed in accordance with the preferred embodiment of the present invention.
Figure 2:
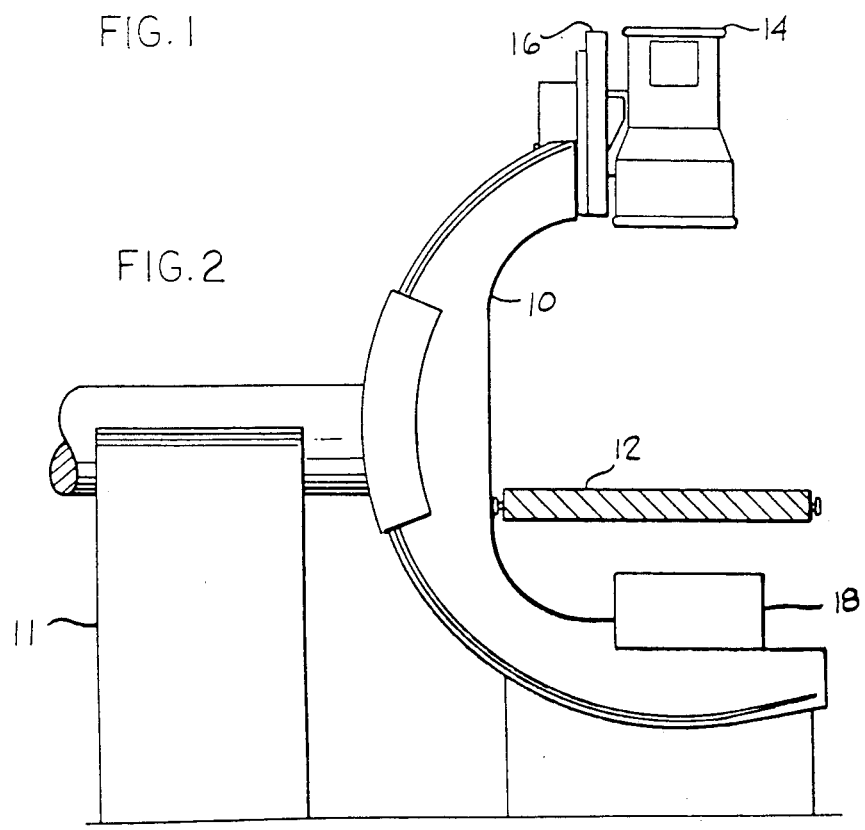
FIG. 2 is a side pictorial diagram of the portion of the X-ray imaging system illustrated in FIG. 1.
Figure 4:
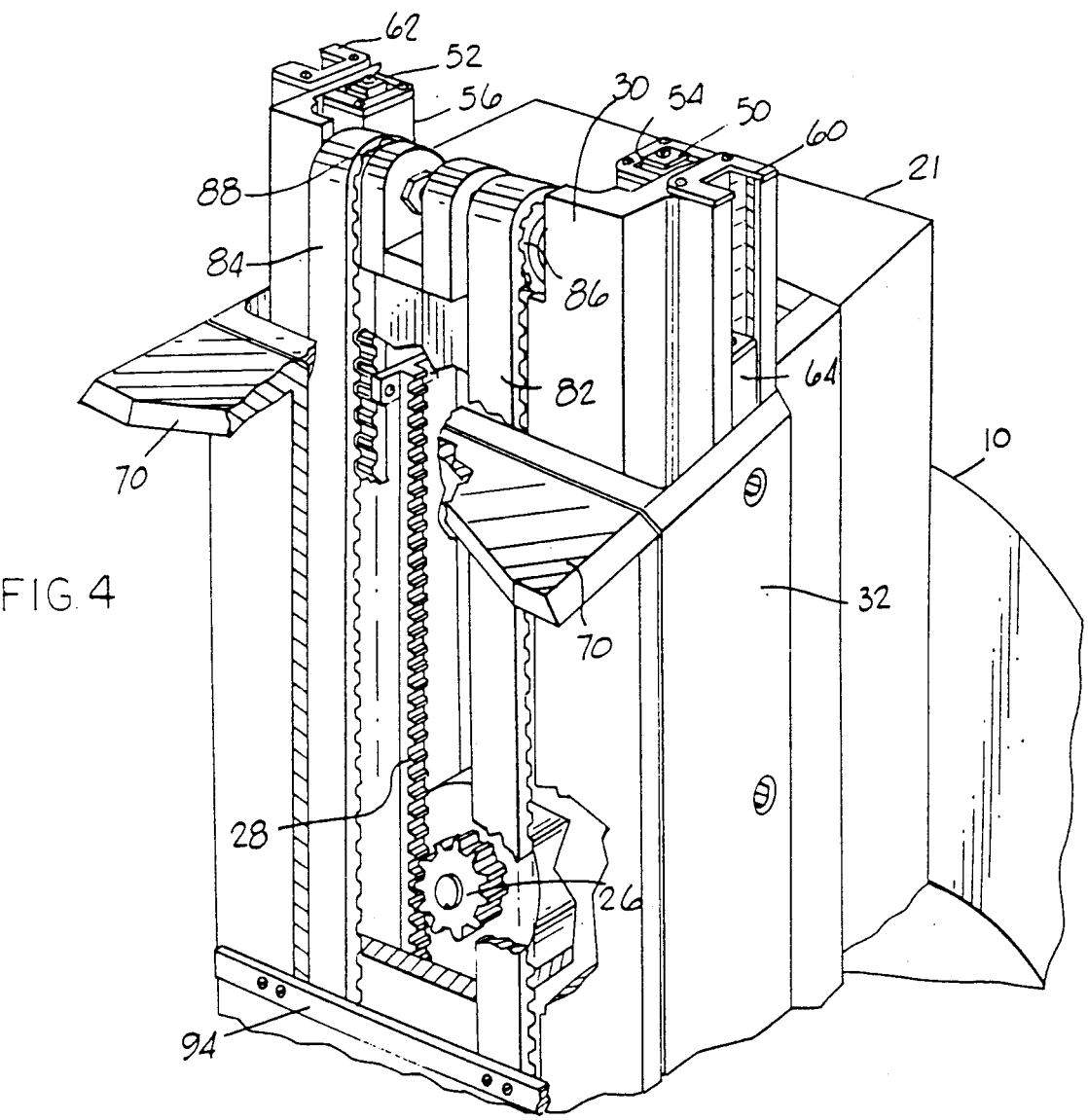
FIG. 4 is a detailed pictorial diagram of a portion of the dual-slide image intensifier support mechanism illustrated in FIGS. 1 and 2.

Referring now to FIGS. 1 and 2, there are shown pictorial diagrams of a portion of an X-ray imaging system that includes a C-shaped arm 10, encompassing a patient table 12, and supported by a pedastal 11 for both arcuate and rotational motion of the C-shaped arm 10, as illustrated. A conventional image intensifier 14 is supported at one end of the C-shaped arm 10 above patient table 12 by a dual-slide support mechanism 16 that provides for bi-directional travel of image intensifier 14 in the vertical directions illustrated. It is important that the top and bottom ends of the dual-slide support mechanism 16 not extend beyond the top and bottom ends of image intensifier 14 when image intensifier 14 is positioned at the center of its permitted range of vertical travel, as illustrated in FIGS. 1 and 2. This restriction results in a compact combination of image intensifier 14 and its support mechanism 16 that will prevent interference with patient table 12 and a patient lying thereon as the C-shaped arm is positioned for parking purposes or to perform a particular procedure. A conventional X-ray tube 18 is supported at the other end of the C-shaped arm 10 below patient table 12 and in general alignment with image intensifier 14.

Figure 3:
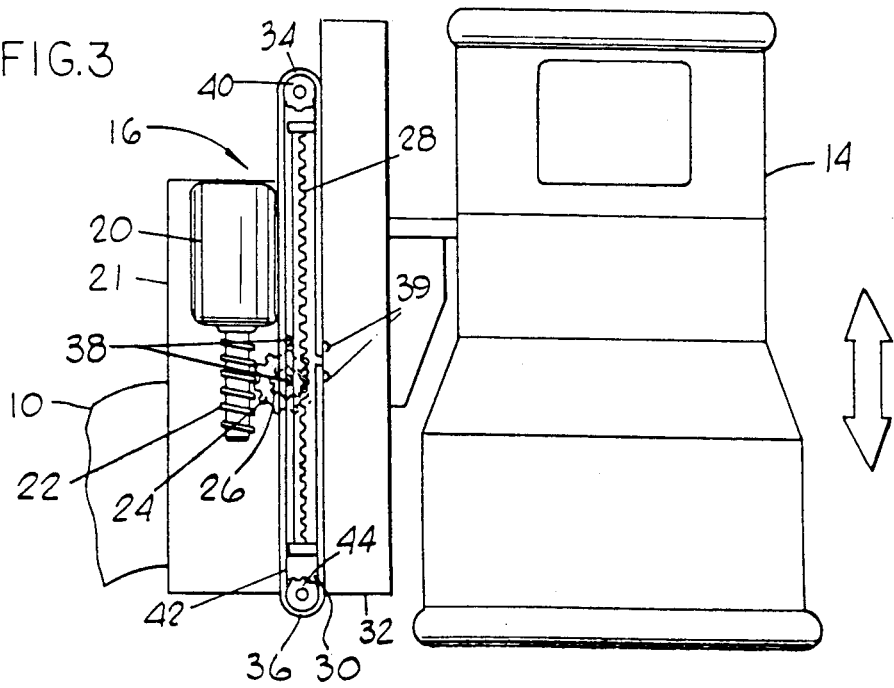
FIG. 3 is a pictorial schematic diagram illustrating the way in which travel of an image intensifier is provided by the dual-slide image intensifier support mechanism of FIGS. 1-3.
Figure 5:
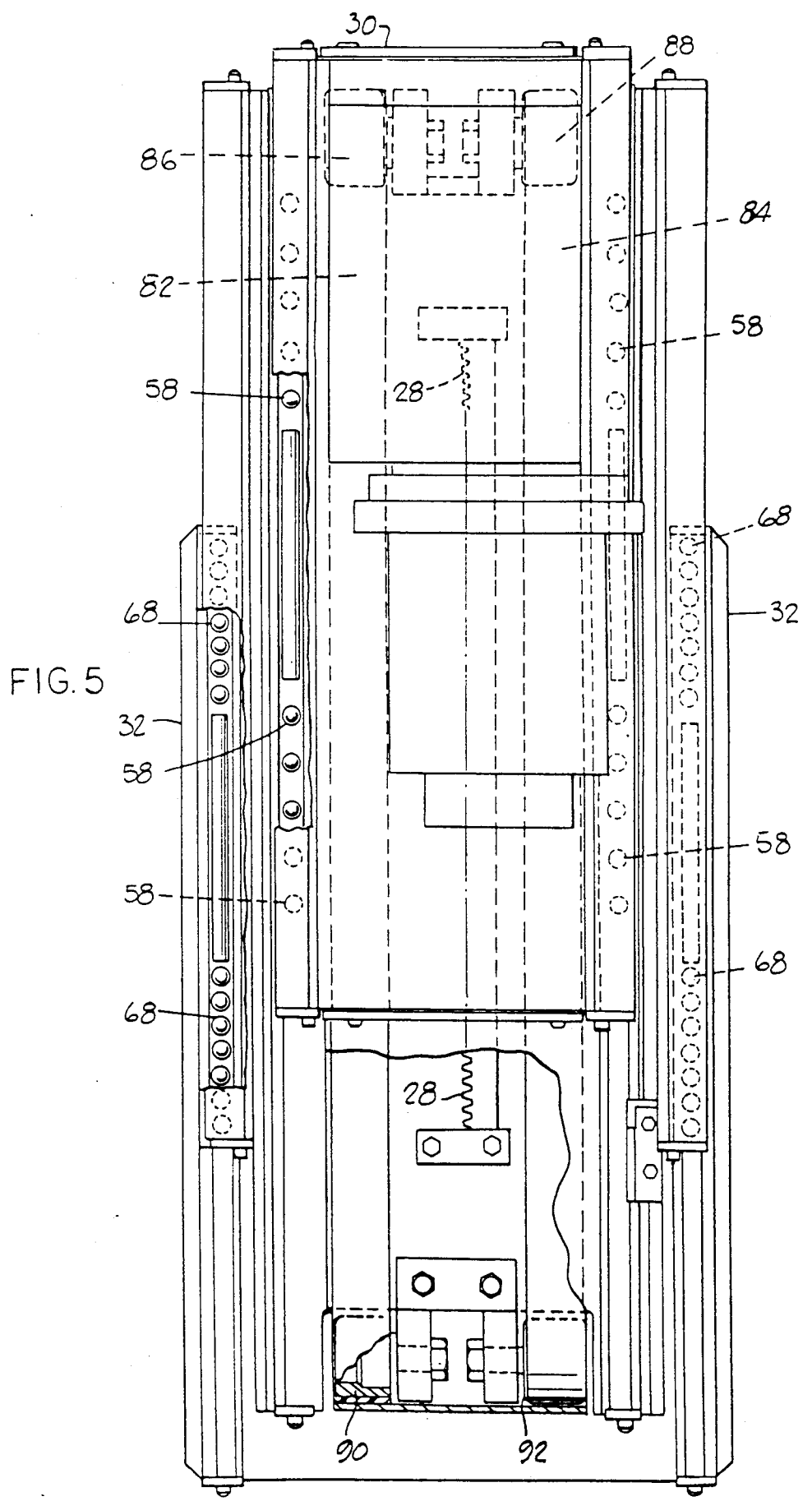
FIG. 5 is a partial sectional diagram illustrating the telescoping relationship between primary and secondary slides of the dual-slide image intensifier support mechanism of FIGS. 1-4.
Figure 6:
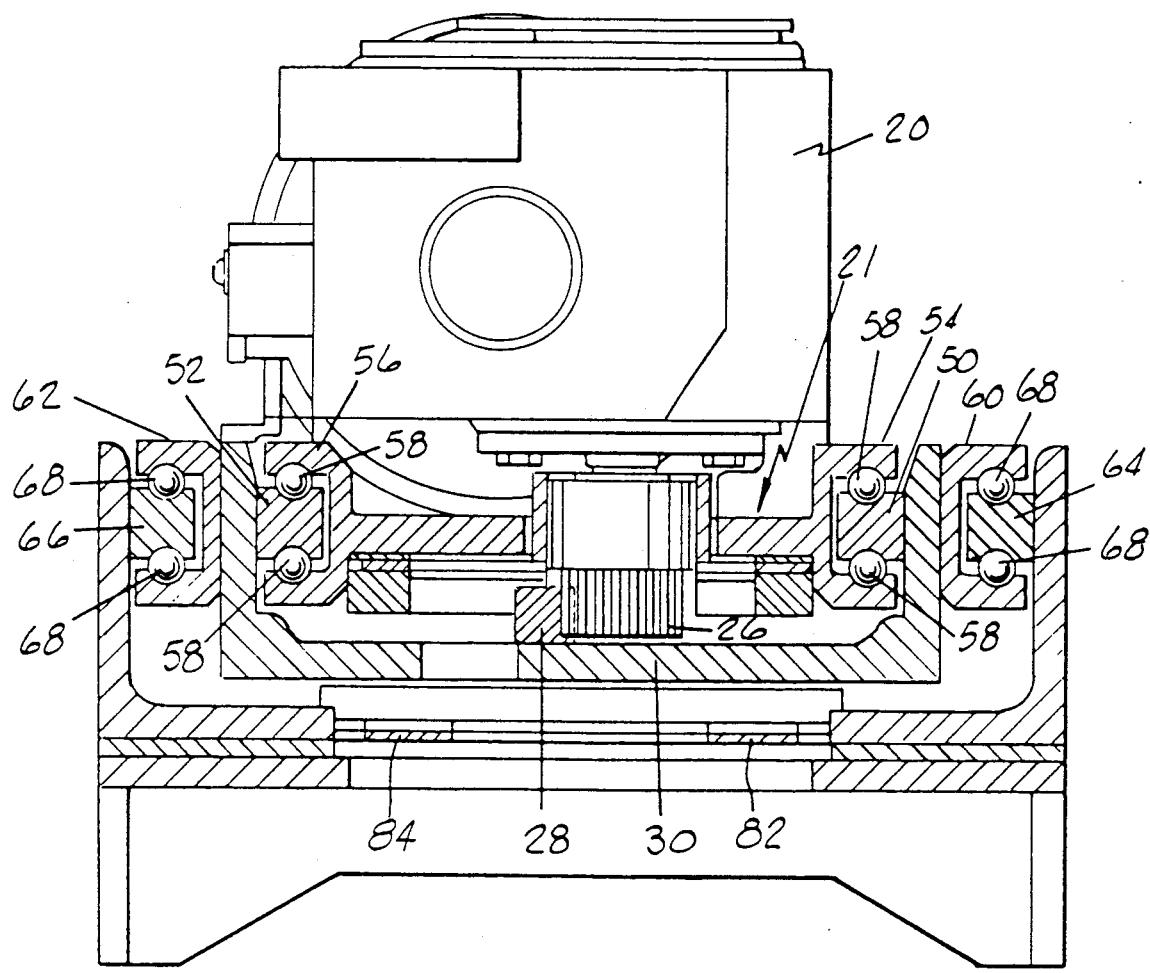
FIG. 6 is a partial sectional top view of the dual-slide image intensifier support mechanism of FIGS. 1-6.

Referring now to FIG. 3, there is shown a pictorial schematic diagram illustrating the way in which the dual-slide support mechanism 16, mounted at one end of C-shaped arm 10, operates to provide bi-directional vertical travel of image intensifier 14 through a range that is approximately double the overall length of the dual-slide support mechanism 16. A motor 20, mounted within a fixed housing 21, includes a worm gear shaft 22 that drives a worm gear reducer 24. Worm gear reducer 24 includes a pinion gear 26 that in turn engages a rack 28 that is mounted to a primary slide 30. Rack 28 extends along substantially the entire length of primary slide 30 to permit a range of travel of primary slide 30 substantially equal to its length. A secondary slide 32 is arranged in sliding engagement with primary slide 30. Image intensifier 14 is fixedly mounted to secondary slide 32. One end of a belt 34 is attached to fixed housing 21 at points 38 that are approximately midway between the top and bottom ends of primary slide 30. Belt 34 is routed upwardly over a pulley 40 mounted near the top end of primary slide 30 and then downwardly between primary slide 30 and secondary slide 32 to points 39 at which it is fixedly attached to secondary slide 32. Similarly, one end of a belt 42 is attached to fixed housing 21 at point 38 and routed downwardly over a pulley 44 that is mounted near the bottom end of primary slide 30 and then upwardly between primary slide 30 and secondary slide 32 to point 39 at which it is also fixedly attached to secondary slide 32. While belts 34 and 42 are illustrated in FIG. 3 as being two separate belts, one of which is routed over the top end of primary slide 30 and the other of which is routed over the bottom end thereof, they could readily be fabricated as a single belt routed over pulleys 40, 44 and attached to fixed housing 21 at point 38 and to secondary slide 32 at point 39 as illustrated.

In operation, rotation of worm gear shaft 22 in a given direction by motor 20 causes pinion gear 26 to impart motion to rack 28 and, hence, primary slide 30 to which it is mounted, in a corresponding direction. Movement of primary slide 30 in turn causes movement of secondary slide 32 in the same direction due to the urging of one end of primary slide 30 against a corresponding one of belts 34, 42. As a result of the mechanical advantage represented by the combination of belts 34, 42 and pulleys 40, 44, incremental travel of primary slide 30 in a given direction results in double that incremental travel in the same direction on the part of secondary slide 32. This mechanical dual-slide arrangement, represented schematically in FIG. 3, thus provides a support mechanism that permits travel of image intensifier 14 over a range that is essentially double the range permitted by the single slide support mechanisms of the prior art while maintaining the overall length of the mechanism within the overall length of image intensifier 14 when image intensifier 14 is positioned in the center of its permitted range of travel.

Referring now to FIGS. 4–7, there is shown the mechanical details of a preferred embodiment of the dual-slide support mechanism of FIGS. 1–3. Fixed housing 21 is attached to C-shaped arm 10. Pinion gear 26, driven by motor 20, engages rack 28 that is fixedly attached to primary slide 30. Primary slide 30 includes a pair of inwardly facing rail members 50, 52 formed on opposite sides thereof. Rail members 50, 52 are received by a pair of outwardly facing U-shaped rail guides 54, 56 formed in fixed housing 21. A multiplicity of ball bearings 58 contained within races formed between rail members 50, 52 and rail guides 54, 56 facilitate sliding motion therebetween, thus permitting sliding motion of primary slide 30 with respect to fixed housing 21.

Primary slide 30 also includes a pair of outwardly facing U-shaped rail guides 60, 62 formed on opposite sides thereof. Secondary slide 32 includes a pair of inwardly facing rail members 64, 66 that are received by U-shaped rail guides 60, 62. A multiplicity of ball bearings 68 contained within races formed between rail members 64, 66 and rail guides 60, 62 facilitate sliding motion therebetween, thus permitting sliding motion of secondary slide 32 with respect to primary slide 30. Secondary slide 32 includes a bracket member 70 for mounting the image intensifier 14 illustrated in FIGS. 1–3.

Motion of secondary slide 32 with respect to primary slide 30 is provided by a pair of belts 82, 84 that are routed upwardly along the front face of primary slide 30, over a pair of pulleys 86, 88 that are mounted near the top end of primary slide 30, and then downwardly along the inner face of primary slide 30 to points 93 at which they are fixedly attached to housing 21. Belt 82, 84 are also routed downwardly along the front face of primary slide 30, over a pair of pulleys 90, 92 mounted near the bottom end of primary slide 30, and the upwardly along the inner face of primary slide 30 to the points 93 at which they are fixedly attached to housing 21. Belts 82, 84 are fixedly attached to secondary slide 32 at points 94 that are is approximately midway between the top and bottom ends of secondary slide 32. Belts 82, 84 may be fabricated of a number of commercial materials such as metal, plastic, fabric, etc. Their inner surfaces may be ribbed, as in the case of a timing belt and as illustrated in FIGS. 4–7, or they may have a smooth inner surface. While belts 82, 84 have also been illustrated in FIGS. 4–7 as being two separate belts routed parallel to each other, they could as well be fabricated as a single belt, with top pulleys 86, 88 being fabricated as a single pulley or roller and bottom pulleys 90, 92 also being fabricated as a single pulley or roller.

Operation of the dual-slide support mechanism illustrated in FIGS. 4–7 is the same as that described above in connection with the schematic diagram of FIG. 3. While the dual-slide support mechanism of the present invention has been described as providing support and extended travel for image intensifier 14, the same mechanism could also provide support and travel for X-ray tube 18, illustrated in FIGS. 1 and 2 as being mounted at the opposite end of C-shaped arm 10 from image intensifier 14.

I claim:

1. An X-ray imaging system mechanism for providing support and bi-directional linear travel for a component of an X-ray imaging system, the mechanism comprising:
   C-shaped arm means, supported by a frame, and adapted for both arcuate and rotational motion with respect to said frame;
   a housing, fixedly attached to one end of said C-shaped arm means;
   primary slide means, coupled to said housing for linear travel with respect to said housing, said primary slide means including first and second roller means positioned at opposite ends of said primary slide means;
   a single motor, coupled to said housing, for bi-directionally driving said primary slide means over a primary range of linear travel;
   secondary slide means, coupled in sliding engagement with said primary slide means, said secondary slide means supporting said component of the X-ray imaging system; and
   belt means, routed over said first and second roller means of said primary slide means, said belt means being fixedly attached to said housing adjacent an outer face of said primary slide means and also being fixedly attached to said secondary slide means adjacent an inner face of said primary slide means, said belt means being operative, in response to incremental travel in a selected direction of said primary slide means initiated by said single motor, for causing simultaneous incremental travel of said secondary slide means in the selected direction, said simultaneous incremental travel of said secondary slide means being double the incremental travel of said primary slide means.

2. An X-ray imaging system mechanism as in claim 1 wherein said component comprises an image intensifier.

3. An X-ray imaging system mechanism as in claim 1 wherein said component comprises an X-ray tube.

4. An X-ray imaging system mechanism as in claim 1 wherein said primary and secondary slide means are substantially equal in length, said length being no greater than an overall length of said component.

* * * * *